United States Patent [19]
Amiot

[11] Patent Number: 5,079,168
[45] Date of Patent: Jan. 7, 1992

[54] CELL CULTURE APPARATUS

[75] Inventor: Bruce P. Amiot, Delano, Minn.

[73] Assignee: Endotronics, Inc., Coon Rapids, Minn.

[21] Appl. No.: 230,400

[22] Filed: Aug. 10, 1988

[51] Int. Cl.$^5$ .............................................. C12M 3/06
[52] U.S. Cl. ..................................... 437/284; 435/288; 435/311; 435/313; 210/321.64; 210/321.76; 210/321.85
[58] Field of Search .................. 435/2, 240.23, 240, 435/241, 242, 240.25, 284-286, 288, 299, 300, 301, 310, 311, 313; 210/321.64, 321.72, 321.75, 321.76, 321.79, 321.8, 321.84, 321.85, 321.88, 321.89; 422/48; 261/122, DIG. 28

[56] References Cited

U.S. PATENT DOCUMENTS

| | | | |
|---|---|---|---|
| 3,450,598 | 6/1969 | Welch et al. | 435/240.23 |
| 3,821,087 | 6/1974 | Knazek et al. | 435/285 |
| 3,843,454 | 10/1974 | Weiss | 435/285 |
| 3,883,393 | 5/1975 | Knazek et al. | 435/284 |
| 3,997,396 | 12/1976 | Delente | 435/285 |
| 4,087,327 | 5/1978 | Feder et al. | 435/285 |
| 4,184,922 | 1/1980 | Knazek et al. | 435/284 |
| 4,200,689 | 4/1980 | Knazek et al. | 435/2 |
| 4,201,845 | 5/1980 | Feder et al. | 435/285 |
| 4,206,015 | 6/1980 | Knazek et al. | 435/2 |
| 4,220,725 | 9/1980 | Knazek et al. | 435/285 |
| 4,225,671 | 7/1980 | Puchinger et al. | 435/285 |
| 4,391,912 | 7/1983 | Yoshida et al. | 435/284 |
| 4,546,083 | 10/1985 | Meyers et al. | 435/285 |
| 4,720,462 | 1/1988 | Rosenson | 435/285 |
| 4,948,732 | 4/1976 | Haddad et al. | 435/285 |

FOREIGN PATENT DOCUMENTS

| | | |
|---|---|---|
| 0263371 | 9/1987 | European Pat. Off. . |
| 8900188 | 1/1989 | PCT Int'l Appl. . |
| 8904865 | 6/1989 | PCT Int'l Appl. . |
| 2164663 | 3/1986 | United Kingdom . |

Primary Examiner—Robert J. Hill, Jr.
Assistant Examiner—William H. Beisner
Attorney, Agent, or Firm—Sughrue, Mion, Zinn, Macpeak & Seas

[57] ABSTRACT

A compact, easily assembled cell culturing device comprising at least one envelope, the interior of which defines a cell culturing space wherein the envelope is spirally wrapped about an elongated core and which provides for optimal gas delivery and removal to and from the cell culturing space which is also separate from nutrient media delivery and removal whereby greater amounts of oxygen are provided to the cells at a faster rate to produce cells and/or cell products more economically and in higher yields.

29 Claims, 6 Drawing Sheets

CELL CULTURE APPARATUS

FIELD OF THE INVENTION

This invention relates to a device for cultivating cells in vitro. More particularly, it relates to a compact easily assembled cell culturing device comprising at least one envelope, the interior of which defines a cell culturing space wherein the envelope is spirally wrapped about an elongated core. The invention relates even more particularly to a cell culturing device, simple in design, yet which provides for efficient gas delivery and removal to and from the cell culturing space to be separate from nutrient media delivery and removal whereby greater amounts of oxygen are provided to the cells at a faster rate to produce cells and/or cell products more economically and in higher yield.

BACKGROUND OF THE INVENTION

The culturing of living cells in vitro is performed for a variety of purposes including the preparation of viral vaccines, the recovery of valuable by-products of cell metabolism and the production of tissue-like derivatives for creating artificial organs.

Several problems are associated with growing living cells in vitro to produce dense masses of cells. First individual components of the nutrient medium must diffuse through the cell layers to reach all cells. This becomes increasingly difficult as the thickness of the cell layer increases.

Second, the maintenance of a suitable environment for cell growth is difficult because the fluid immediately adjacent a growing cell is continuously changing as cellular metabolism proceeds and is returned to its original status only in stepwise fashion when the nutrient medium is changed or agitated en masse.

Third, a lattice or suitable material upon which to grow some types of cells is required.

Various types of apparatus and methods have been developed in response to these needs. One method involves attaching and growing cells on the interior surface of plastic or glass roller tubes and bottles as disclosed in U.S. Pat. No. 3,450,598. Another method involves attaching the cells to a flat surface of stationary containers such as petri dishes or rectangularly shaped culture plates. The flat surfaces can be stacked one on top of each other in a spaced-apart array as disclosed in U.S. Pat. No. 3,843,454.

The use of hollow fibers or synthetic capillaries has more recently been disclosed as a support matrix for the propagation of cells. For example. U.S. Pat. Nos. 3,821,087; 3,883,393; 4,184,922; 4,200,689; 4,206,015 and 4,220,725, all to Knazek et al, variously disclose apparatus and methods for the in vitro growth of cells on semi-permeable, tubular membranes or capillaries wherein cells are initially allowed to settle onto the outer surfaces of the capillary walls in a nutrient medium. Nutrients diffuse from the perfusing medium through the capillary walls and are utilized by the cells. Cell products diffuse from the cells through the capillary walls and into the perfusate, from which cell products may be recovered.

U.S. Pat. No. 4,184,922 and 4,200,689 disclose cell culturing devices comprising a single bundle of fibers wherein some of the fibers are connected to one perfusion circuit and the remaining fibers are connected to a second perfusion circuit. The difference in pressure between the two circuits produces convective currents of perfusate within the extracapillary space and thereby improves nutrient distribution to the growing cells.

In U.S. Pat. No. 4,220,725, a bundle of capillaries, upon which cells are allowed to grow, is wrapped in a porous envelope or sheet material which creates an extra-envelope space into which the cells can migrate for periodic removal without disturbing the main cell culture. The creation of the extra-envelope space increases the surface area for nutrient end waste product diffusion to and from the cells located on the outer surface of the capillaries.

In U.S. Pat. No. 3,997,396, cells are attached to and grown on one side or surface of a single hollow fiber membrane wherein the cells are propagated and maintained by passing oxygen through the membrane from the side opposite that to which the cells are attached and into contact with the cells while simultaneously incubating the cells in a nutrient medium. By continuously passing oxygen through the membrane from the side opposite that on which the cells are attached, a continuous and uniform supply of oxygen reaches and nourishes the cells thereby facilitating aerobic propagation of the cells in the desired tissue densities.

In U.S. Pat. Nos. 4,087,327 and 4,201,845 to Feder et al, an in vitro cell culture reaction system is disclosed which utilizes elongate hollow or solid fibers arranged in a shallow layer configuration as a matrix for cell attachment on the outer surface of the fibers. Nutrient media flow is directed substantially uniformly through the fiber layer and substantially transverse to the plane of the elongate axes of the fibers. The cells are aerated by passing oxygen through the interior of the fibers which then permeates the fiber walls. The use of a shallow bed of fibers in a relatively short path of media flow results in a substantial reduction of the nutrient and metabolic product gradients that is normally produced by the fibrous bundle as well as a more extensive utilization of the fiber surface for cell attachment.

U.S. Pat. No. 4,391,912 discloses a device for cultivating floating animal cells comprising a gas permeable shell and a plurality of hollow fibers enclosed within the shell, wherein the hollow fibers are open at either end outside of the shell and have a pore diameter of from about $10^2$ angstroms to $5 \times 10^4$ angstroms. Nutrient medium passes through the interior of the hollow fibers and oxygen passe through the shell and the animal cells are cultivated in the space between the shell and the hollow fibers. These pore diameters of the hollow fibers are disclosed as optimizing efficient exchange of nutrients and metabolic products produced by the cells resulting in high density cell growth.

Notwithstanding the usefulness of the hollow fiber cell culture devices, it has been found that the nutrient media flow through the hollow capillaries prevents complete penetration of the capillary bundle by the cells and sets up an undesirable gradient of medium flow. As a result, there is an incomplete utilization of the available capillary surface for cell attachments and cells become unevenly distributed along the surface. Also, as the nutrient medium flows through the reactor, nutrients are more available to the cells near the inlet, and as the medium flows to the outlet, metabolic products such as lactic acid accumulate in the medium, undesirably affecting pH and producing other toxic effects on the cells.

Another significant difficulty encountered with these hollow fiber-type cell culture devices concerns the high media circulation rates necessary to supply adequate oxygen to the cells. Specifically aqueous nutrient media, equilibrated with air, is able to carry 4.5 ml of oxygen per liter (37° C. 760 mm of Hg). This relative inability of aqueous solutions to carry oxygen causes the rate at which oxygen is supplied to the cells to be the limiting step in vitro cell growth operations. In order to produce high yields of cells and/or cell secreted products, media circulation rates must be increased to provide more oxygen to cells. High circulation rates in turn cause high internal pressure and turbulence which has presented problems in terms of constructing the device on an industrial scale and in propagating mammalian cells whose sensitivity and fragility prohibit the use of too vigorous aeration and/or agitation. Vigorous aeration also causes the denaturation of many biologically and medicinally useful proteins produced by cell cultures.

Moreover, the above-described hollow fiber-type devices which provide for separate oxygen and nutrient media delivery to cells suffer from the additional disadvantages of being mechanically complex, difficult to assemble and being unduly large. Moreover, the dimensions of these devices are not constrained to maintain the growing cells in close proximity to the nutrient media supply source thus causing undesirable nutrient gradients.

Therefore, it has been desirable to provide new cell culturing devices for growing cells in vitro, particularly mammalian cells, which overcome the various difficulties associated with the prior art devices and produce cells and/or cell secreted products more economically and in higher yields.

SUMMARY OF THE INVENTION

It is thus an object of the present invention to provide an improved cell culturing device which overcomes the above-mentioned difficulties associated with the prior art.

It is another object of the present invention to provide a cell culturing device for in vitro cell propagation which features optimally efficient gas exchange between the cells and the external environment achieved by delivering and removing gas to and from the cells separately from nutrient media.

It is a further object of the present invention to provide a cell culturing device which allows for dramatically reduced nutrient media circulation rates, thereby affording greater ease in industrial scale-up.

It is an even further object of the present invention to provide a cell culturing device which is simple in design easy to assemble, compact in size and has a gentle internal environment in which to grow cells and recover cells and/or valuable cell products in high yields.

These and other objects of the present invention are realized in a cell culture device in one embodiment comprising:

(a) at least one envelope having first and second external surfaces wherein the envelope comprises a first membrane layer sealed to a second membrane layer along their first and second lateral and longitudinal edges, respectively, to define a cell culturing space therebetween;

(b) a first delivery means for delivering nutrient media to the cell culturing space:

(c) a second delivery means for delivering cells to the cell culturing space (d) a third delivery means for delivering gas to the cell culturing space (e) an elongated core having a longitudinal axis, to which a first lateral edge of the envelope is attached parallel to the axis, and about which the envelope is spirally wrapped, such that the longitudinal edges are disposed in two planes perpendicular to the longitudinal axis of the core (f) an adhesive means disposed along the entire length of both of the longitudinal edges of the first external surface of the at least one envelope such that when the envelope is spirally wrapped about the core, the longitudinal edges of the first external surface fixedly adhere to the core and then to the second external surface of a previously wound layer of envelope whereby a spirally extending inter-envelope gas space is created therebetween:

(g) a first removal means for removing metabolic waste products from the cell culturing space;

(h) a second removal means for removing cells and/or cell products from the cell culturing space (i) a third removal means for removing gaseous waste products from the cell culturing space:

(j) a first end header means disposed adjacent to a first end of the core and having inlet means in communication with the delivery means: and (k) a second end header means disposed adjacent to a second end of the core and having outlet means in communication with at least one of the removal means.

BRIEF DESCRIPTION OF THE DRAWINGS

The advantages and features of the present invention will be more fully understood from the following description of the preferred embodiments, taken in conjunction with the accompanying drawings. wherein.

DETAILED DESCRIPTION OF THE PREFERRED EMBODIMENTS

In the various embodiments of the invention as illustrated in the drawings, like structures will be referred to by like reference numerals.

Figure 1:
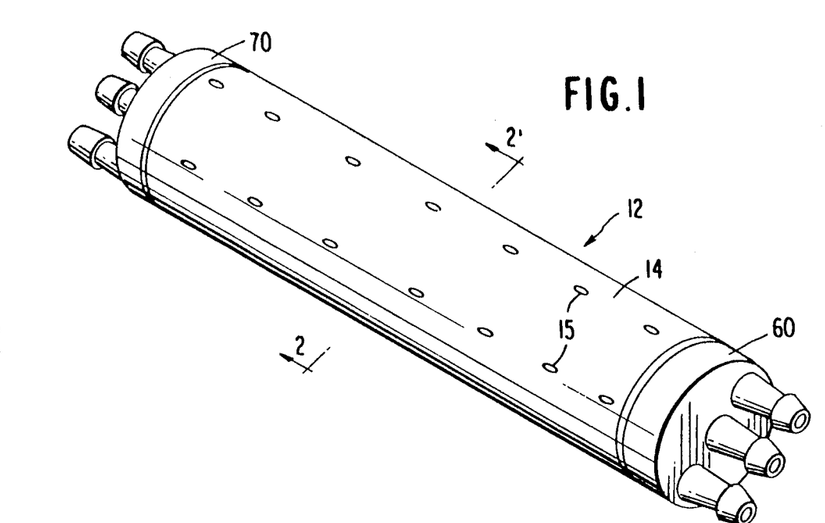
FIG. 1 is a perspective view of the cell culturing device of the present invention in assembled condition according to a first embodiment.

In the embodiment of the invention as shown in FIG. 1, an assembled cell culturing device is provided as generally indicated at 12. In this embodiment, the cell culturing device 12 includes an outer shell or jacket 14 which is preferably an elastomeric sleeve made of silicone or a heat shrinkable thermoplastic sleeve, the surface of which has perforations 15. Shell 14 and the end cap headers 60 and 70 together form an exterior enclosure of the cell culturing device 12.

Figure 2:
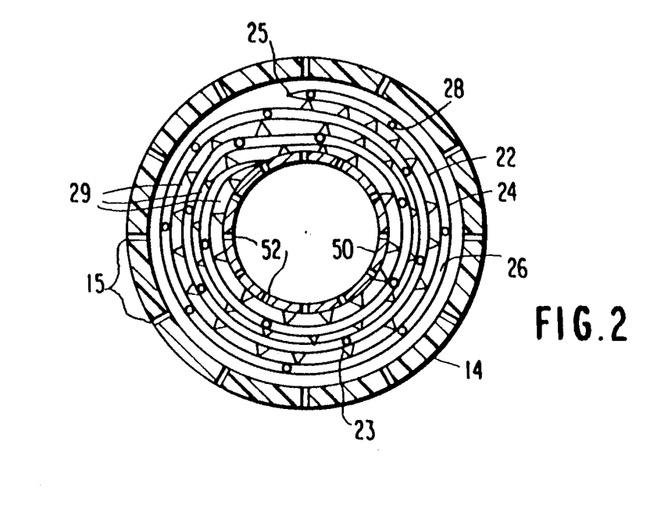
FIG. 2 is a cross-sectional view taken along the line 2—2' in FIG. 1.

FIG. 2 is a cross-sectional view of the first embodiment of the invention as illustrated in FIG. 1. The specific features of this figure will be described upon reference to FIG. 3, described in detail hereinafter.

Figure 3:
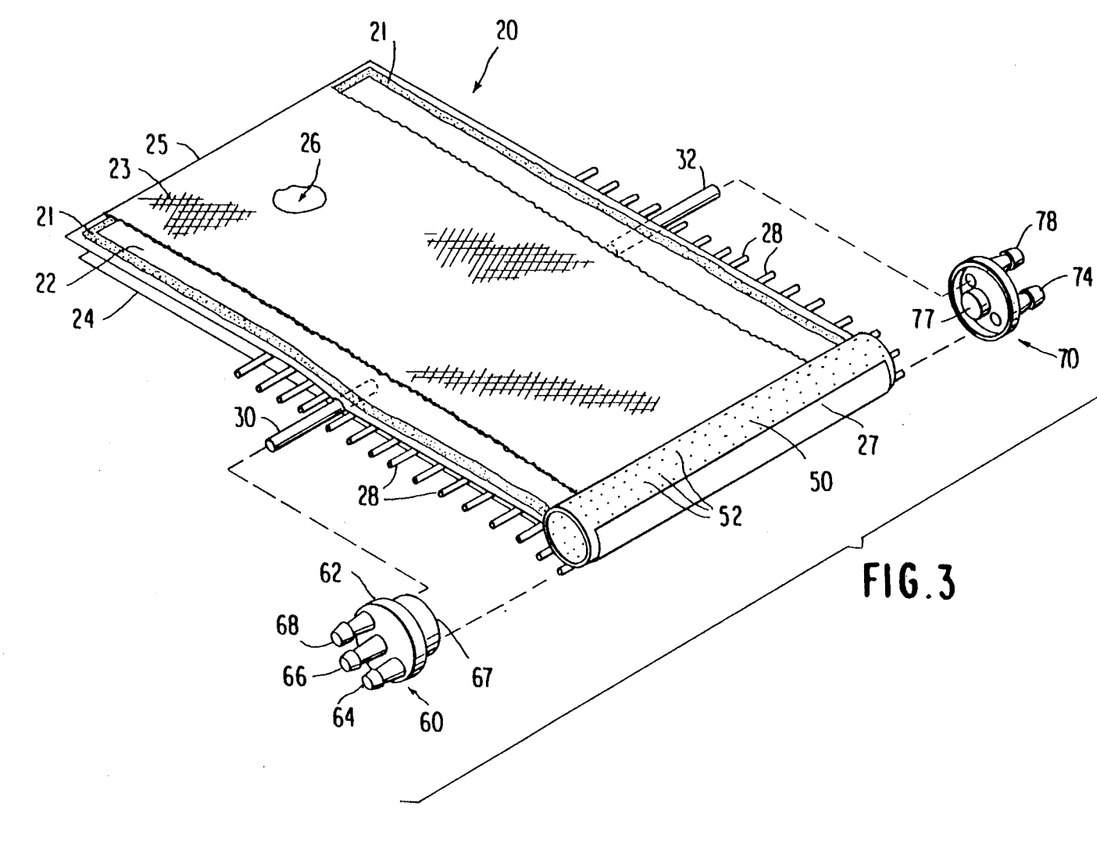
FIG. 3 is an exploded perspective view of a first embodiment of the present invention in its unassembled state.

Turning now to FIG. 3, which illustrates a first embodiment of the present invention in its unassembled state, a cell culturing envelope 20, having first and second external surfaces which are defined by first and second membrane layers 22 and 24, respectively, having substantially equal dimensions and which are sealed to each other along their first and second longitudinal edges and first and second lateral edges, respectively, with a suitable adhesive 21 to define a cell culturing space 26 therebetween. Silicone adhesives are preferred. The layers 22 and 24 are preferably made of a porous hydrophobic material such as medical-grade silicone, micro-porous polyethylene, polysulfone, polycarbonate or polyethylene which is permeable to gases such as air, oxygen and carbon dioxide but impermeable to cells and liquids. The porous membrane layers generally have a pore size in the range from about 0.02 to 0.4 microns. A preferred material is medical-grade silicone because it does not require additional chemical or physical modifications of its surface to permit the effective attachment of cells thereto and provides for optimally efficient gas exchange between the cell culturing space 26 and the external environment. A particularly preferred material is a fabric-reinforced polymethylsiloxane produced by SciMed Life Systems of Minneapolis, Minn. and by Dow Corning of Midland, Mich. under the name "SILASTIC". Membrane layers 22 and 24 should also be constructed to be as thin as possible to minimize their resistance to gas diffusion. For example, when silicone is used as the membrane material, a suitable thickness is about 0.125 mm. A preferred thickness of the layer material is in the range of from about 0.1 mm to 0.250 mm. The above-mentioned hydrophobic materials are also advantageous in that they do not allow water films to form on their surface which increases resistance to gas diffusion. The longitudinal length of the envelope, relative to an external circumference of the core 50, should allow for a plurality of layers of envelope to be spirally wrapped about the core. In practice, the longitudinal length of the envelope may be from about 1 m to 90 m, preferably from about 2 m to 40 m and its lateral length or width is generally in the range from about 0.1 m to about 0.3 m, and preferably from about 0.15 m to about 0.25 m.

In this embodiment, nutrient media is delivered to and water-soluble waste products are removed from the cell culturing space by a plurality of hollow fibers or capillaries 28 having liquid permeable walls, which are disposed within the envelope and whose open ends extend outwardly from between the sealed longitudinal edges of the envelope such that the capillaries communicate with the cell culturing space only through the walls of the capillaries. The capillaries can be disposed in the envelope substantially equally spaced from and parallel to each other. The distance between the capillaries is generally from about 100 microns to about 1000 microns; the preferred distance is from about 200 microns to about 500 microns. A distance of less than 100 microns is difficult from a manufacturing point of view and does not allow adequate space for cell growth. Spacing of more than 1000 microns tends to cause nutrient gradients to develop in the cell culturing space which, as discussed above, results in less than optimal cell and/or cell product yield. The capillaries can be produced from any suitable material which is non-toxic to cells and which can be spun into fibers which form a semi-porous, hydrophilic, and selectively permeable membrane wall. Examples include cellulose acetate, anisotropic polysulfone, polyethersulfone, saponified cellulose ester, nylon, polyacrylonitrile and acrylic copolymers. A preferred material is "CUPROPHAN", a regenerated cellulose acetate manufactured by Enka Ltd., Del Ray, CA. The capillaries 28 transport fresh nutrient media containing glucose, amino acids, vitamins and other essential nutrients necessary for specific cell metabolism requirements to the cells. The media diffuses through the capillary walls into the cell culturing space 26. Cellular waste products diffuse from the cell culturing space 26 into the capillaries 28 and are carried away by the media flowing therethrough. The external diameter of the capillaries 28 is generally in the range from about 60 to 400 microns, preferably from about 200 microns to 300 microns; the internal diameter is generally from about 100 to 300 microns, preferably from about 200 microns to about 250 microns.

Figure 4:
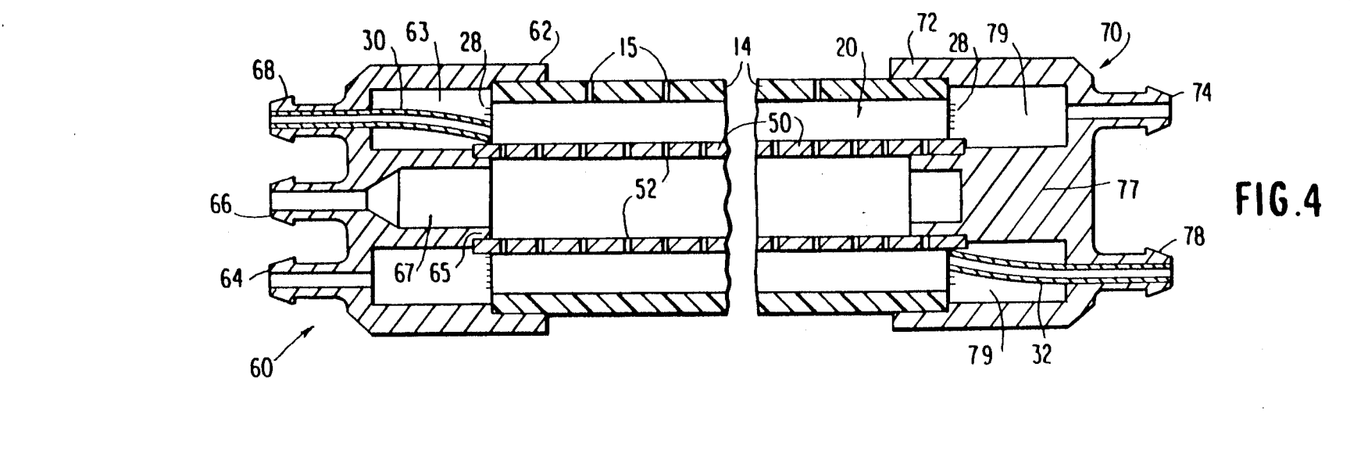
FIG. 4 is a longitudinal sectional view of an assembled device according to a first embodiment of the present invention.

Access into the cell culturing space 26 for both the delivery of cells and the removal of cells and/or cell products is provided by entry and exit tubes 30 and 32, respectively. Tube 30 is disposed between the first longitudinal edges of the layers 22 and 24 of the envelope and projects into the cell culturing space such that a first end portion of the tube communicates with the cell culturing space and a second end portion of the tube communicates with extra-capillary inlet port 68 on the first end cap header 60 as illustrated in FIG. 4 discussed below. Tube 32 is disposed between the second longitudinal edges of the layers 22 and 24 of the envelope opposite the edges which tube 30 is disposed such that tube 32 projects into the cell culturing space whereby a first end portion of the tube communicates with the cell culturing space and a second end portion of the tube communicates with extra-capillary outlet port 78 on the second end cap header 70 as illustrated in FIG. 4. The entry and exit tubes may be constructed of a flexible biocompatible material such as silicone rubber, polyethylene or polyurethane. A preferred material is silicone rubber. The internal diameter of the tubes should be sufficiently large to allow for adequate cell inoculation into the cell culturing space and the removal of cells and/or cell products therefrom. A suitable internal diameter is generally in the range from about 1.5 mm to about 9.5 mm. The external diameter of the tubes is selected to facilitate bonding or sealing of the tubes 30 and 32 between the longitudinal edges of membrane layers 22 and 24 which comprise envelope 20. A preferred external diameter is about 3 mm to about 13 mm. Tubes 30 and 32 extend far enough into the cell culturing space 26 merely to provide for adequate cell inoculation and cell and/or cell product harvesting, respectively. Although not shown in FIG. 3, more than one of each of tubes 30 and 32 may be appropriately disposed in the envelope.

Upon assembly of envelope 20 having a plurality of capillaries 28 and at least one of each of tubes 30 and 32 disposed therein, an adhesive 21 is applied along the entire length of both longitudinal edges and along a first lateral edge 27 of a first external surface of the envelope. Then, a support mesh 23 in the form of a sheet having dimensions such that its longitudinal and lateral edges are substantially close to but do not contact the adhesive 21 is superimposed on the first external surface of the envelope. The mesh preferably comprises a nonwoven plastic screen having a thickness of from about 0.5 mm to about 1.0 mm. Next, as illustrated in FIG. 3, the first lateral edge 27 is adhesively attached to an elongated core 50 parallel to the longitudinal axis of the core. Envelope 20 is then spirally wrapped about the core such that the longitudinal edges of the envelope are disposed in two planes perpendicular to the longitudinal axis of the core and such that the longitudinal edges of the first external surface of the envelope fixedly adhere to the core and, once having completely covered the external circumferential surface of the core with one wrap, fixedly adhere to the longitudinal edges of a second external surface of the previously wrapped layer of envelope The envelope, when spirally wrapped about the core in this manner, forms a spirally extending inter-envelope space 29 having the mesh 23 contained therein, as illustrated in FIG. 2, described in detail below. Inter-envelope space 29 allows for the unrestricted and spirally outward flow of gaseous waste products which have diffused thereinto from the cell culturing space through membrane layers 22 and 24. The mesh functions to maintain the inter-envelope space by preventing adjacently wrapped layers of envelope from coming into contact with each other as cell culturing space 26 becomes filled with nutrient media and the cell density increases. The inter-envelope space can be maintained in alternative ways besides the use of the mesh as will be apparent to one of ordinary skill in the art.

The elongated core 50 in this embodiment of the invention serves a dual purpose. First, the core functions as a support for the spirally wrapped envelope. Second, the core serves as a gas permeable conduit through which gas is allowed to flow along the entire longitudinal length of the core and diffuse radially outward therefrom. Therefore, the core is suitably made of a material sufficient rigid to provide support for the envelope as well as being sufficiently porous to permit the flow of gas therethrough such as a plastic, metal or alloy. As illustrated in FIG. 3, the core can be made of a hollow, rigid material whose surface is perforated with openings or pores 52 to permit the diffusion of gas therefrom. The pore size is generally in the range of from about 0.5 mm to 5 mm and preferably from about 1.25 mm to 2.50 mm. Although not shown in the drawings, the core can alternatively be made of a porous solid material such as microporous polyethylene, ceramic or other sintered material.

After the envelope is completely wrapped about the core, the wrapped sub-assembly can be optionally fitted with a shell or jacket 14 such as a heat shrinkable thermoplastic sleeve as illustrated in FIGS. 1 and 2. Suitable examples of materials which can be used include PVC (polyvinylchloride), polyolefin, TEFLON, MYLAR, polyethylene and KYNAR (polyvinylidene fluoride). Of course, in this embodiment, if a protective shell is provided as shown, it must either be gas permeable and/or perforated (as shown in FIGS. 1 and 2) to allow for the escape of gas from the device. A second function of the shell or jacket is to constrain the spirally wrapped envelope, so that once filled with a nutrient medium, the cell culture chamber located between the sheets 22 and 24 will have a total thickness of no greater than from about 200 to about 500 microns, preferably no greater than from about 200 to 350 microns.

Once the envelope is wrapped about the core and encased within a shell in the above-described manner, a first end cap header 60 is disposed adjacent a first end of the core as illustrated in FIG. 4. Annular shoulder or flange 62 of header 60 is fixedly attached to the external circumferential edge of shell 14 to form a hydraulic seal therewith. Extra-capillary inlet port 68 is adapted to receive cell inoculation tube 30 so as to be in fluid communication therewith. Gas inlet port 66 is attached to a pump or a compressed gas apparatus external to the device for the supply of air to the device and is adapted at the interior thereof to engage a first end of the core to be in fluid communication therewith and provide for the unrestricted flow of a gas such as air into the core. In this embodiment, an auxiliary header 67 is adapted to gas inlet port 66 and whose annular shoulder 65 engages the open end of core 50 so as to be in fluid communication therewith. As used herein, the term "air" is construed to mean not only atmospheric air but also gases and mixtures thereof which are non-toxic and physiologically acceptable to cells and which are conducive to their growth in vitro. Alternatively, auxiliary header 67 can be replaced by a plastic tube which is adapted at its first and second ends to be in communication with the gas inlet port and the open end of the core, respectively. Intra-capillary inlet port 64 is attached to an external nutrient media supply source and is adapted at the interior of the device to communicate with plenum chamber 63 which is defined by end cap header 60, auxiliary header 67 and the plane defined by the surface of core 50 perpendicular to its longitudinal axis and the first longitudinal edges of each successively wrapped layer of envelope which are sealed to each other. Plenum chamber 63 communicates with first open ends of capillaries 28 which extend outwardly from the sealed longitudinal edges of the envelope and into the chamber. It is preferred that the capillaries are cut flush with the above-described plane.

A second end cap header 70 is disposed adjacent a second end of the core such that annular shoulder or flange 72 of header 70 fixedly attaches to the external circumferential edge of the shell 14 to form a hydraulic seal therewith. Of course, if a shell were not provided, annular shoulders or flanges 62 and 72 would be fixedly attached to the external circumferential edge of the outermost spirally wrapped layer of envelope. Extra capillary outlet port 78 is adapted at the interior of the device to receive product harvest tube 32 for the removal of cells and/or cell products from cell culturing space 26. Plug 77, attached to header 70, engages the interior circumferential surface of core 50 to prevent the escape of gas therefrom. Of course, plug 77 need not be attached to header 70 but can be supplied separately. Alternatively, a suitable cap can be fitted onto the end of core 50 in a fluid-tight fashion or the core can be constructed to have a sealed second end. Intra-capillary outlet port 74 is adapted at the interior of the device to communicate with plenum chamber 79 which is defined by header 70, plug 77 and the plane defined by the surface of core 50 perpendicular to its longitudinal axis and the second longitudinal edges of each successively wrapped layer of envelope which are sealed to each other, and into which the second open ends of capillaries 28 extend.

Fresh nutrient media is caused to flow into the device through intra-capillary inlet port 64 into plenum chamber 63 which then perfuses through the capillaries via the first open ends thereof. Media and nutrients diffuse through the capillary walls into cell culturing space 26 and are taken up by the cells. Used media and water-soluble cellular metabolic waste products then diffuse from cell culturing space 26 through the capillary walls and are carried by the perfusing media from capillaries 28 into plenum chamber 79 and out of the device through intra-capillary outlet port 74.

Gases are supplied to and removed from the device in the following manner. As illustrated in FIG. 4, air is caused to flow into the device through gas inlet port 66 and auxiliary header 67 into core 50. Turning now to FIG. 2, air flows through pores 52 into inter-envelope space 29 and flows spirally therethrough and diffuses through membrane layers 22 and 24 into cell culturing space 26 and is taken up by the cells. Gaseous waste products diffuse through membrane layers 22 and 24 into inter-envelope space 29 and are caused to flow spirally therethrough and outward from core 50 through a space defined by the second lateral edge 25 of envelope and the previously wrapped layer which are unsealed. Gas exits the device by flowing through openings 15 on shell or jacket 14.

Figure 5:
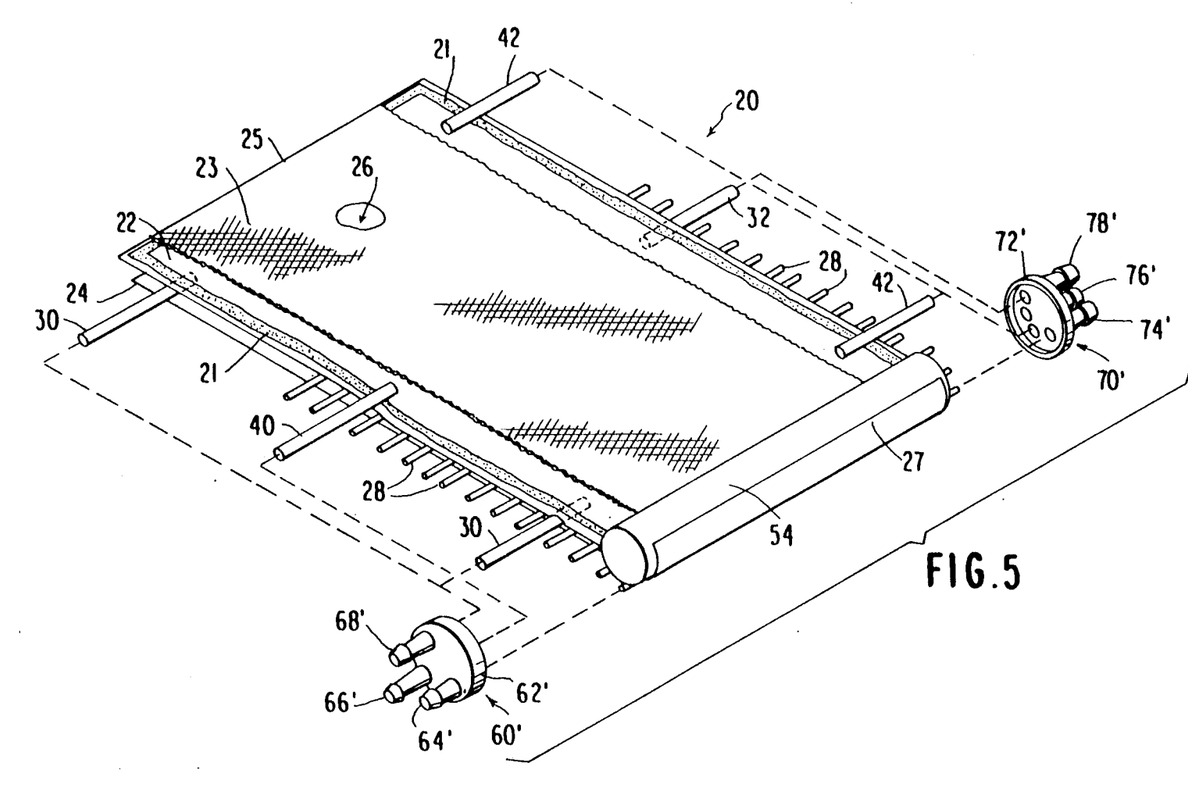
FIG. 5 is an exploded perspective view of a second embodiment of the present invention in its unassembled state.
Figure 6:
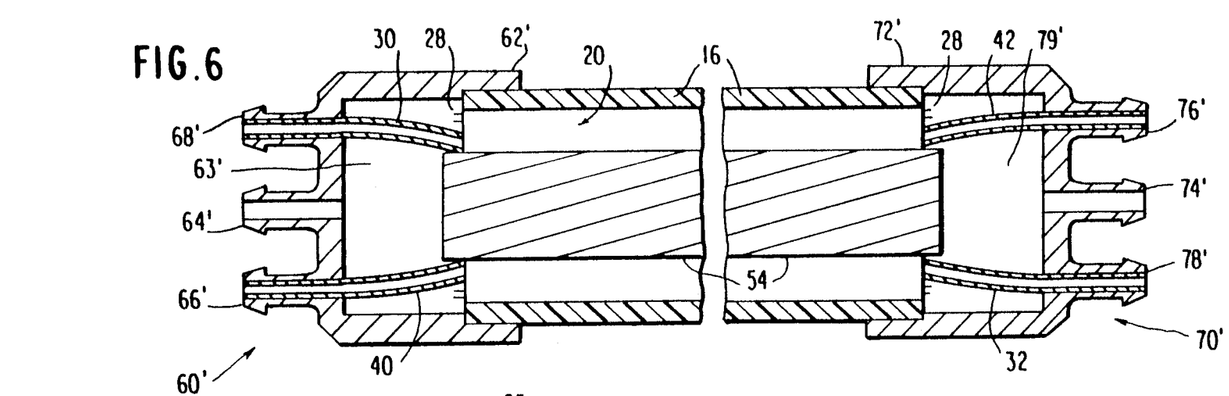
FIG. 6 is a longitudinal sectional view of an assembled device according to a second embodiment of the present invention.
Figure 7:
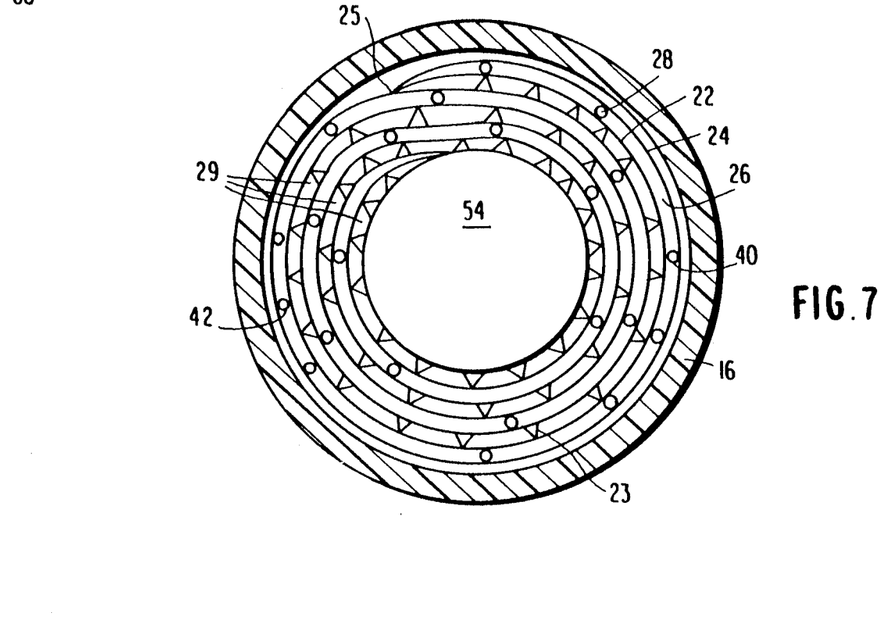
FIG. 7 is a cross-sectional view similar to the cross-sectional view of FIG. 2, but showing the arrangement for the second embodiment.

A second embodiment of the invention is illustrated in FIGS. 5-7. This embodiment differs from the first embodiment in several respects, all of which relate to the way in which gases are supplied to and removed from the growing cells in the cell culturing space.

In FIG. 5, envelope 20 having disposed therein capillaries 28 and tubes 30 and 32 is assembled as described above. Next, adhesive 21 is applied along the entire length of the first and second longitudinal and lateral edges of the first external surface of envelope 20. Then, at least one gas inlet tube 40 is disposed on and secured to the first external surface of envelope 20 and which extends along at least a portion of the surface thereof so as to be parallel with the longitudinal axis of core 54 and which also extends outwardly from the envelope such that when the envelope is spirally wrapped about the core and the device is fully assembled, one open end of tube 40 is easily adapted to communicate with gas inlet port 66' on end cap header 60 and whose other open end communicates with inter-envelope gas space 29, illustrated in FIG. 7, discussed below. Disposed on and secured to the opposite longitudinal edge of the first external surface of envelope 20 is at least one gas outlet tube 42 which also extends along at least a portion of the surface thereof and which also extends outwardly from the envelope such that when the envelope is spirally wrapped about the core and the device is fully assembled, one open end of tube 42 is easily adapted to communicate with the gas outlet port 76' on header 70, and the other open end communicates with inter-envelope gas space 29. Mesh 23 is then superimposed on the first external surface of envelope 20 in the same manner as described above. First lateral edge 27 of envelope is adhesively attached to core 54. The core in this embodiment is impermeable to gases and can be comprised of any material which accomplishes this purpose and which also provides support for the spirally wrapped envelope. Envelope 20 is then spirally wrapped in the same manner as described above except that upon the completion of the wrapping, the second lateral edge 25 of envelope 20 having adhesive 21 supplied thereon adheres to the second external surface of the previously wrapped layer of envelope. This wrapped assembly can then be optionally fitted with a shell 16, as illustrated in FIGS. 6 and 7 described below. In this embodiment, the shell can be a heat shrinkable thermoplastic sleeve as in the first embodiment but is different in that it need not be permeable to gases and/or perforated. In this embodiment, the shell insures that the cells in cell culture space 26 will be no further than from about 100 microns to about 250 microns from an oxygen source which in this embodiment is the space, interenvelope space 29 which is supplied with oxygen by tube 40.

Once the envelope is wrapped about the core and encased within shell 16 in the above-described manner, a first end cap header 60' is disposed adjacent a first end of core 54 as illustrated in FIG. 6. Annular shoulder or flange 62' of header 60' is fixedly attached to the external circumferential edge of shell 16 to form a hydraulic seal therewith. Extra-capillary inlet port 68' is adapted to receive cell inoculation tube 30 to be in fluid communication therewith. Gas inlet port 66' is attached to a pump or a compressed gas means external to the device for the supply of air to the device and is adapted at the interior of the device to engage gas inlet tube 40 to be in fluid communication therewith and provide for the unrestricted flow of a gas such as air therethrough. Intra-capillary inlet port 64' is attached to a nutrient media supply source or reservoir external to the device and is adapted at the interior thereof to communicate with plenum chamber 63' which is defined by header 60 and the plane defined by the surface of core 54 perpendicular to its longitudinal axis and the first longitudinal edges of each successively wrapped layer of envelope which are sealed to each other. Plenum chamber 63, communicates with first open ends of the capillaries 28 which extend outwardly from the sealed longitudinal edges of the envelope and into the chamber. A second end cap header 70' is disposed adjacent a second end of the core such that annular shoulder or flange 72' of header 70' fixedly attaches to the external circumferential edge of the shell 16 to form a hydraulic seal therewith. Of course, as per the first embodiment, if a shell were not provided, annular shoulders or flanges 62' and 72' would be fixedly attached to the external circumferential edges of the outermost spirally wrapped layer of envelope. Extra-capillary outlet port 78' is adapted at the interior of the device to be in fluid communication with product harvest tube 32 for the removal of cells and/or products from cell culturing space 26. Intra-capillary outlet port 74' is adapted at the interior of the device to communicate with plenum chamber 79' which is defined by header 70 and the plane defined by the surface of core 54 perpendicular to its longitudinal axis and the second longitudinal edges of each successively wrapped layer of envelope which are sealed to each other, and into which the second open ends of capillaries 28 extend. Gas outlet port 76' is adapted at the interior of the device to be in fluid communication with gas outlet tube 42 for the removal of gaseous waste products from the device.

Nutrient media is caused to flow into and out of the device substantially in the manner described above for the first embodiment.

Gases are caused to enter and exit the device in the following manner. As illustrated in FIG. 6, air is caused to flow from an air supply source external to the device not shown and into the device through gas inlet port 66' and then into gas inlet tube 40. Turning now to FIG. 7 gas flows from tube 40 into inter-envelope gas space 29 and diffuses through membrane layers 22 and 24 into cell culturing space 26 where oxygen is taken up by the cells. Gaseous waste products diffuse through membrane layers 22 and 24 and into inter-envelope gas space 29. Turning back to FIG. 6, gases then flow through gas outlet tube 42 and exit the device through gas outlet port 76' on header 70' which is in fluid communication with gas outlet tube 42.

In this embodiment, although only one of each of tubes 40 and 42 is shown, the number of gas inlet tubes 40 is desirably one greater than the number of gas outlet tubes 42. It is also preferred that they be arranged along opposite longitudinal edges of the first external surface of the envelope in an alternating fashion. Of course gas inlet port 66 and gas outlet port 76' would be adapted at the interior of the device to engage a plurality of tubes 40 and 42, respectively, in a manner known to those skilled in the art.

This embodiment is advantageous in that an oxygen gradient is not created in the cell culturing space 26 such that cells growing in the area of the cell culturing space disposed farthest from the external surface of the core are not deprived of the oxygen necessary for growth.

In the above-described embodiments of this invention, cells can be grown by initially allowing them to attach to the walls of the hollow fibers and the interior surfaces of the envelope or by allowing them to "float" between the hollow fibers as disclosed in U.S. Pat. No. 4,391,912.

Figure 8:
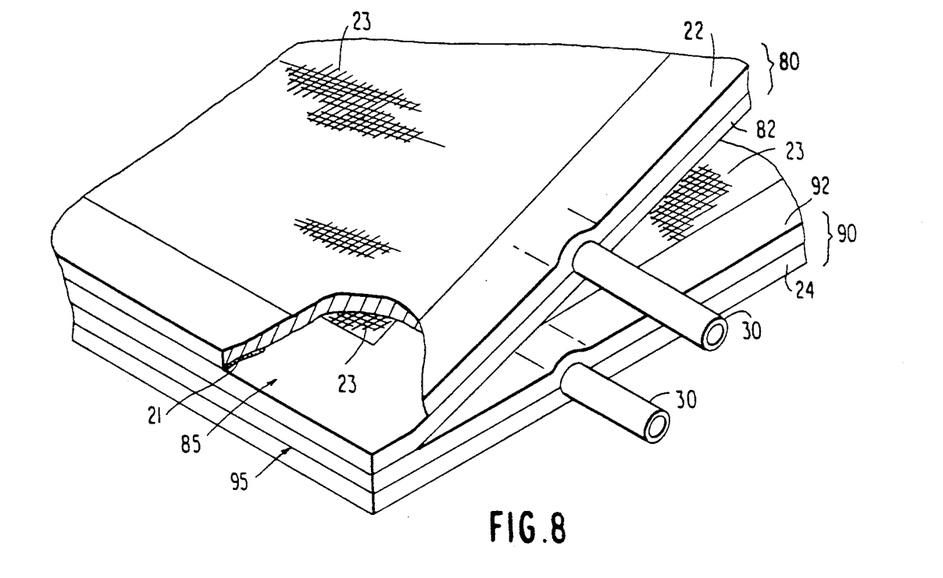
FIG. 8 is a detailed perspective view of a third embodiment of the present invention.

A third embodiment of the present invention is illustrated in FIGS. 8–11. This embodiment is similar to the second embodiment; however, it differs from the second embodiment in several significant ways. First, as shown in FIG. 8, two envelopes 80 and 90 are provided. Each envelope is formed by superimposing and bonding a gas-permeable hydrophobic membrane layer 22 and 24 onto a semi-porous hydrophilic membrane layer 82 and 92 respectively, with a suitable adhesive 21 placed along all four edges of at least one membrane layer thereby forming cell culture space 85 and 95, respectively, therebetween, Suitable materials for the gas-permeable hydrophobic layers include those mentioned above in the description of the first embodiment. Suitable materials for the semi-porous hydrophilic layers includes those used to make the capillaries as described above. Cell inoculation tube 30 and product harvest tube 32 are disposed within envelopes 80 and 90 as described above for the first two embodiments. It is noted that in this embodiment of the present invention, capillaries are not used. A mesh 23 as described above is then placed atop membrane layers 22, 82, 92 and 24. Then, envelope 80 is superimposed on envelope 90 such that membrane layers 82 and 92 face one another and are bonded together along both their lateral edges with a suitable adhesive. Their longitudinal edges remain unsealed.

Figure 9:
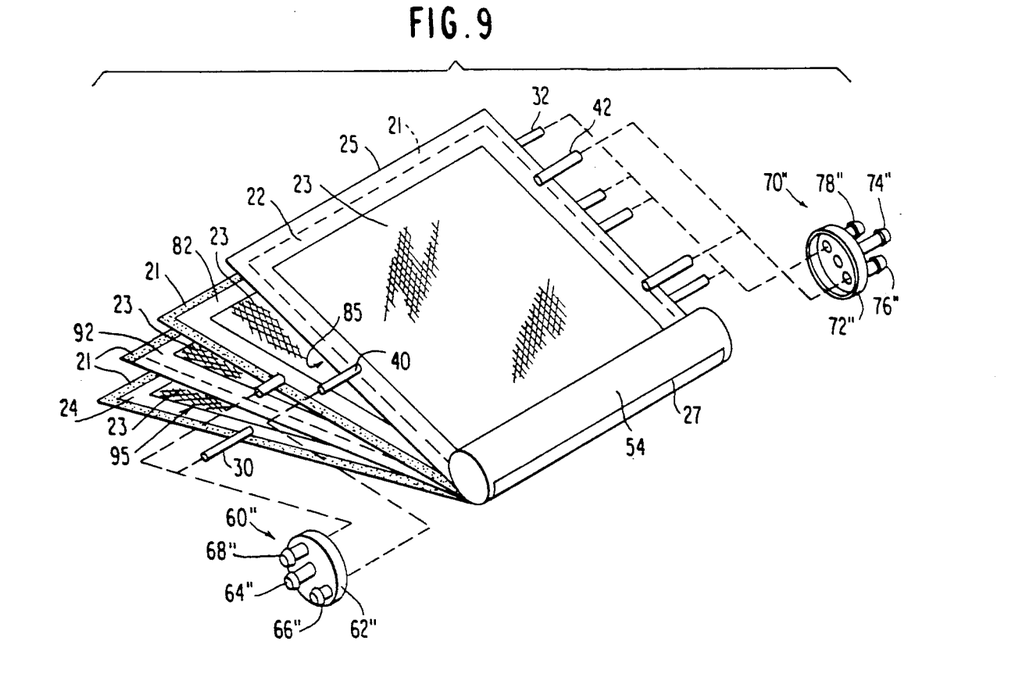
FIG. 9 is an exploded perspective view of a third embodiment of the present invention in its unassembled state.

Turning now to FIG. 9, a suitable adhesive is applied to first and second longitudinal and lateral edges of the external surface of layer 22. Then, gas inlet tubes 40 and gas outlet tubes 42 are disposed on and secured to the external surface of layer 22 as described above for the second embodiment. A first lateral edge of layer 22 is attached to core 54 along its longitudinal surface. The core in this embodiment is substantially the same as described for the second embodiment.

Figure 10:
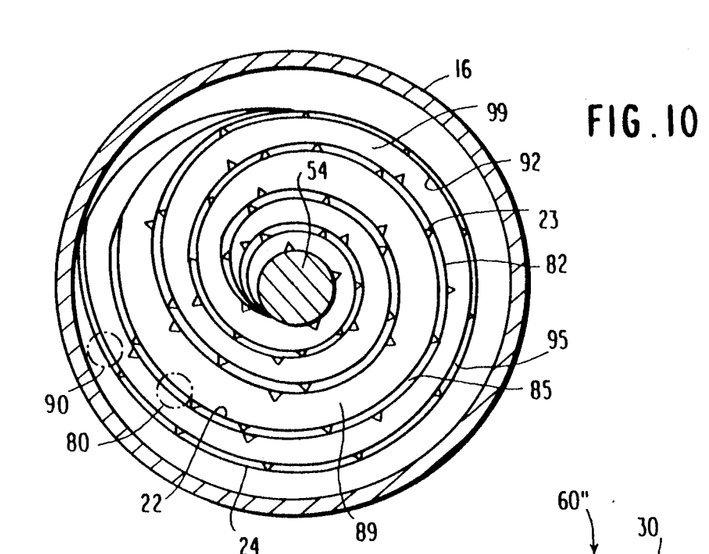
FIG. 10 is a cross-sectional view similar to FIG. 2, but showing the arrangement for the third embodiment.

Envelopes 80 and 90, assembled and adhered to each other as described, are spirally wrapped about core 54 where upon completion of the wrapping, the second lateral edge 25 of layer 22 adheres to the external surface of layer 24 of the previously wrapped layer of envelope. This is illustrated in FIG. 10. Also, spirally extending inter-envelope space 89 and spirally extending inter-envelope channel 99 are created, each having mesh contained therein for the purpose of maintaining adequate space for gas and media flow, respectively. Inter-envelope space 89 is defined by the adjacent spirally wrapped layers 22 and 24 whose lateral and longitudinal edges are sealed to each other. Channel 99 is defined by adjacent spirally wrapped layers 82 and 92 whose longitudinal edges are unsealed and whose lateral edges are sealed.

Figure 11:
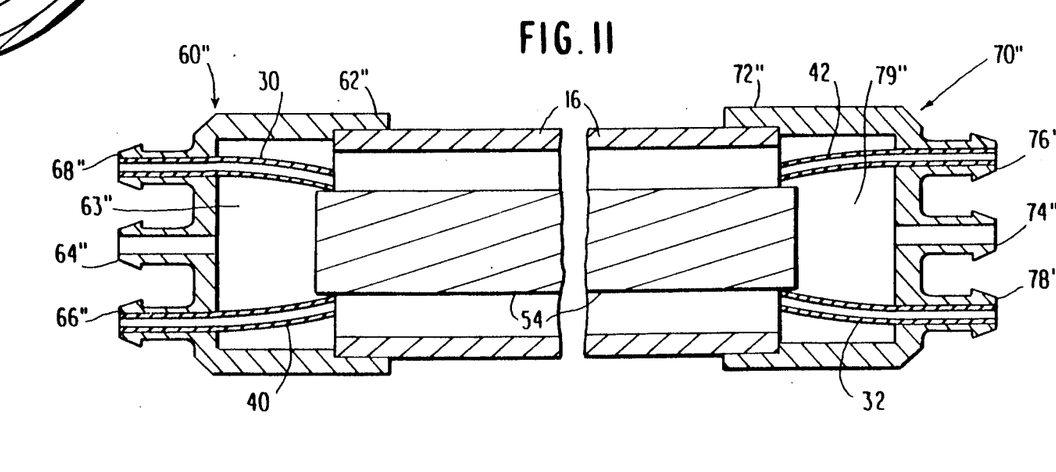
FIG. 11 is a longitudinal sectional view of an assembled device according to a third embodiment of the present invention.

The wrapped sub-assembly can then be optionally fitted with a jacket or shell 16 and then have first and second end cap headers 60" and 70" engage first and second ends, respectively, of shell 16 as described above for the second embodiment and as illustrated in FIG. 11.

Fresh nutrient media is caused to flow into the device from an external media supply source through inlet port 64" and into plenum chamber 63" which is defined by end cap header 60" and the plane defined by the surface of core 54 perpendicular to its longitudinal surface and the first longitudinal edges of each successively wrapped layer of envelopes 80 and 90. Nutrient media then flows into channel 99 (illustrated in FIG. 10) which is in fluid communication with chamber 63''', between the unsealed adjacent spirally extending longitudinal edges of layers 82 and 92, and diffuses into cell culture spaces 85 and 95 respectively, where it is taken up by the cells. Used media and water soluble metabolic waste products diffuse from cell culturing spaces 85 and 95 through membrane layers 82 and 92, respectively, into channel 99 and are carried by perfusing media into a second plenum chamber 79" defined by end cap header 70" and the plane defined by the surface of core 54 perpendicular to its longitudinal axis and the second longitudinal edges of each successively wrapped layer of envelopes 80 and 90 and which is in fluid communication with channel 99. Nutrient media exits the device by flowing through outlet port 74" which is in fluid communication with chamber 79'''.

Gases are supplied to and removed from the device substantially as described for the second embodiment and as illustrated in FIGS. 10 and 11. As shown in FIG. 11, air flows into the device through gas inlet port 66" which is adapted at the interior of the device to be in fluid communication with gas inlet tubes 40. Turning now to FIG. 10, gas flows through tubes 40 into inter-envelope space 89 and diffuses into cell culture spaces 85 and 95 through membrane layers 22 and 24, respectively, and is taken up by the cells. Gaseous waste products exit cell culturing spaces 85 and 95 by diffusing through membrane layers 22 and 24, respectively, and into inter-envelope space 89. Turning back to FIG. 11, gases then flow through tubes 42, adapted to be in fluid communication with gas outlet port 76" on end cap header 70" and exits the device therethrough. In FIG.

11, only one of each of tubes 40 and 42 are shown because they are coplanar with each other.

Thus, this embodiment of the present invention also provides for the separate supply and removal of nutrient media and gases to and from the cells yet without the use of capillaries.

Any of the three embodiments hereinbefore described can be modified in the following way. To increase the amount of surface area in the cell culturing space for the cells to attach, any positively charged non-toxic particles of from about 200 to 400 microns in diameter such as microcarriers, reticulated polyurethane foam or silica particles can be added to the cell culturing space and enclosed therein upon assembly of the envelope.

A wide variety of different types of animal cells can be cultured in the device of this invention including, for example, amphibian, mammalian and avian cells, particularly mammalian cells. Examples thereof include human lung fibroblast cells, Rhesus monkey kidney cells, vero cells, MDCK cells, Chinese hamster ovary cells, chick fibroblast cells mouse embryo fibroblast cells and baby hamster kidney cells. Bacterial cells, Insect cells, and Plant cells can also be cultured therein but this invention is particularly applicable to culture of animal cells as listed above.

The device is also adapted to be used with any conventional nutrient media such as Eagle's basal medium Dulbecco's modified minimum essential medium (MEM) and Earle's or Hank's balanced salt solutions fortified with appropriate nutrients, fetal calf sera, and other materials.

By providing a gas such as oxygen to the cells in the manner described according to the present invention, cells can be grown more economically and cells and/or cell products can be produced in higher yields because the rate at which oxygen is delivered to the cells is greatly increased over what it is in prior art devices. For example, aqueous nutrient media equilibrated with air can carry only 4.5 ml of oxygen per liter of 37° C. and 760 mm Hg pressure while air under the same conditions can carry 209 ml of oxygen per liter. Thus, at least 46 (209/4.5) times more oxygen is available from a liter of air than a liter of water. Moreover, since a gas such as air is less viscous than water, at any given pressure, a greater amount of air per unit time can be delivered to the cell culturing device, thus maintaining a high oxygen gradient. Therefore, in the present invention, the increase in cells and/or cell product can be at least 10 to 46 times the yield obtained in conventional devices. Also, the fluid flow rate of the non-aerated media can be decreased to be in the order of from 100 to 1000 ml of media per hour per square meter of cell culturing device. It is noted that existing cell culturing devices operate in the order of 500 ml of media per minute per square device in order to supply the amount of oxygen necessary for cell growth. This reduction in flow rate and the commensurate reduction in internal pressure facilitate industrial scale-up.

Although the present invention has been described in detail and with reference to specific embodiments, thereof, it will be apparent to one skilled in the art that changes may be made in form and detail without departing from the spirit and scope of the invention.

What is claimed is:

1. A cell culture device comprising:
   (a) at least one envelope having first and second external surfaces each having first and second lateral and longitudinal edges wherein the envelope comprises a first membrane layer sealed to a second membrane layer along said first and second lateral and longitudinal edges, respectively, to define a cell culturing space therebetween, said first and second membrane layers being porous and substantially permeable to gases but substantially impermeable to cells and liquids;
   (b) a first delivery means for delivering nutrient media to the cell culturing space;
   (c) a second delivery means for delivering cells to the cell culturing space;
   (d) a third delivery means for delivering a gas to the cell culturing space through said first and second membrane layers;
   (e) an elongated core having a longitudinal axis, means sealing one of said lateral edges of one of said membrane layers to said core parallel to the axis of said core, said envelope being spirally wrapped about said core such that said longitudinal edges are disposed in two planes perpendicular to the longitudinal axis of the core;
   (f) an adhesive means disposed along the entire length of both the longitudinal edges of the first external surface of the at least one envelope such that the longitudinal edges of the first external surface fixedly adhere to the core and then to the second external surface of said envelope, and spacer means between each layer of envelope whereby a spirally extending interenvelope gas space is created therebetween;
   (g) a first removal means for removing liquid metabolic waste products from the cell culturing space;
   (h) a second removal means for removing cells, cell products or cells and cell products from the cell culturing space;
   (i) a third removal means for removing gaseous waste products from the cell culturing space through said first and second membrane layers;
   (j) a first end header means disposed adjacent to a first end of the core and having inlet means in communication with at least one of the delivery means; and
   (k) a second end header means disposed adjacent to a second end of the core and having outlet means in communication with at least one of the removal means.

2. A cell culture device according to claim 1, wherein said membrane layers have a pore size of from about 0.02 to 0.4 microns.

3. A cell culture device according to claim 1, wherein said second delivery means comprises at least one tube means disposed between said first longitudinal edges of said first and second membrane layers comprising said envelope and projecting into said cell culturing space such that a first end portion of said tube means communicates with said cell culturing space and a second end portion of said tube means communicates with said inlet means on said first end header means.

4. A cell culture device according to claim 1, wherein said second removal means comprises at least one tubular means disposed between said second longitudinal edges of said first and second membrane layers comprising said envelope, and which projects into said cell culturing space such that a first end portion of said tube means communicates with said cell culturing space and a second end portion of said tube means communicates with said outlet means on said second end header means.

5. A cell culturing device according to claim 1, wherein said spacer means comprises a non-woven plastic screen.

6. A cell culture device according to claim 1, wherein each of said membrane layers comprise medical-grade silicon.

7. A cell culture device according to claim 6, wherein each of said membrane layers has a thickness of from about 0.125 mm to 0.250 mm.

8. A cell culturing device according to claim 1, wherein an outermost layer of said spirally wrapped envelope is disposed within a shell means.

9. A cell culturing device according to claim 30, wherein said shell means comprises a heat shrinkable thermoplastic sleeve.

10. A cell culture device according to claim 1, wherein said first delivery means and said first removal means comprise a plurality of capillaries having liquid permeable walls disposed within said envelope and open ends extending outwardly from between sealed longitudinal edges of said envelope such that said capillaries communicate with said cell culturing space only through the walls of said capillaries.

11. A cell culture device according to claim 10, wherein said capillaries are disposed substantially equally spaced and substantially parallel to each other.

12. A cell culture device according to claim 11, wherein said capillaries are spaced from one another at a distance of from about 100 microns to about 1000 microns.

13. A cell culture device according to claim 10, wherein said core is gas permeable.

14. A cell culture device according to claim 13, wherein said core comprises a hollow material, the circumferential surface of which is perforated.

15. A cell culture device according to claim 8, wherein said third delivery means includes means on said first header means sealingly engaging said core at a first end thereof so as to provide communication between said core and said inlet means on said first end header means.

16. A cell culture device according to claim 13, wherein a second end of said core opposite a first end is sealed with a sealing means to prevent the escape of gas therefrom.

17. A cell culture device according to claim 13, wherein said third removal means comprises an opening defied by said second lateral edge of said envelope and said second external surface of said envelope through which gaseous waste products may exit said device.

18. A cell culture device according to claim 13, wherein said device is disposed within a shell means which is substantially permeable to gases, is perforated, or is substantially permeable to gases and is perforated.

19. A cell culture device according to claim 1, wherein said adhesive means is further disposed along the entire length of said second lateral edge of said first external surface of said envelope such that said edge fixedly adheres to said second external surface of the envelope.

20. A cell culture device according to claim 19, wherein said core is impermeable to gases.

21. A cell culture device according to claim 19, wherein said third delivery means comprises at least one tubular means disposed on and secured to said first external surface of said at least one envelope and which extends at least along a portion of said first external surface so as to be parallel with said longitudinal axis of said core and which also extends outwardly from said envelope to communicate with said inlet means on said first end header means.

22. A cell culture device according to claim 19, wherein said third removal means comprises at least one tubular means disposed on and secured to said first external surface of said at least one envelope and which extends along at least a portion of said first external surface and which also extends outwardly from said envelope so as to communicate with said outlet means on said second end header means.

23. A cell culture device according to claim 19, wherein said first delivery means and said first removal means comprises a plurality of capillaries disposed within said envelope and whose open ends extend outwardly from between said sealed longitudinal edges of said envelope such that said capillaries communicate with said cell culturing space only through the walls of said capillaries.

24. A cell culture device according to claim 23, wherein said first end header means includes a first plenum chamber which communicates with open ends of said capillaries.

25. A cell culture device according to claim 23, wherein said second end header means includes a second plenum chamber which communicates with opposite open ends of said capillaries.

26. A cell culture device comprising:
(a) a first envelope and a second envelope having substantially equal dimensions, each of said envelopes comprising a first membrane layer and a second membrane layer, each of said membrane layers having first and second lateral and longitudinal edges, said first membrane layer being sealed to said second membrane layer along said first and second lateral and longitudinal edges, respectively, so as to define a cell culturing space therebetween, wherein said first membrane layer is a gas-permeable hydrophobic membrane layer and defines a first external surface of each of said envelopes, and wherein said second membrane layer is a semi-porous hydrophilic membrane layer, said first envelope being superimposed upon said second envelope such that said hydrophilic membrane layer of said first envelope faces said hydrophilic membrane layer of said second envelope and is bonded thereto along their first and second lateral edges thereof;
(b) a first delivery means for delivering nutrient media to the cell culturing space of said first envelope and said second envelope through said hydrophilic membrane layers;
(c) a second delivery means for delivering cells to the cell culturing space of said first envelope and said second envelope;
(d) a third delivery means for delivering a gas to the cell culturing space of said first envelope and said second envelope through said hydrophobic membrane layers;
(e) an elongated core having a longitudinal axis, means sealing one of said lateral edges of said first external surface of said first envelope to said core parallel to the axis of said core, said envelopes being spirally wrapped about said core such that said longitudinal edges are disposed in two planes perpendicular to the longitudinal axis of the core;
(f) an adhesive means disposed along the entire length of both the longitudinal edges of said first external surface of said first envelope such that the longitudinal edges of said first external surface of said first envelope fixedly adhere to the core and said first external surface of said second envelope, and spacer means positioned between said first external surface of said first envelope and said first external surface of said second envelope whereby a spirally extending inter-envelope gas space is created therebetween;

(g) a first removal means for removing liquid metabolic waste products from the cell culturing space of said first envelope and said second envelope through said hydrophilic membrane layers;

(h) a second removal means for removing cells, cell products or cells and cell products from the cell culturing space of said first envelope and said second envelope;

(i) a third removal means for removing gaseous waste products from the cell culturing space of said first envelope and said second envelope through said hydrophobic membrane layers;

(j) a first end header means disposed adjacent to a first end of the core and having inlet means in communication with at least one of the delivery means; and (k) a second end header means disposed adjacent to a second end of the core and having outlet means in communication with at least one of the removal means.

27. A cell culture device according to claim 26, wherein said hydrophilic membrane layer comprises regenerated cellulose acetate.

28. A cell culture device according to claim 26, wherein said first delivery means and said first removal means comprise a spirally extending channel defined between adjacent hydrophilic membrane layers of said first envelope and said second envelope such that nutrient media is allowed to flow therethrough from between said first and second unsealed longitudinal edges thereof.

29. A cell culture device according to claim 26, wherein said third delivery means and said third removal means are disposed on and secured to an external surface of said gas-permeable hydrophobic membrane layer of one of said first envelope and said second envelope.

* * * * *